United States Patent [19]
Kristen et al.

[11] Patent Number: 6,034,258
[45] Date of Patent: Mar. 7, 2000

[54] POLYMERIZATION CATALYSTS CONTAINING β-DIKETIMINATE LIGANDS

[75] Inventors: Marc Oliver Kristen, Limburgerhof; Hans-Helmut Görtz, Freinsheim, both of Germany; Berth-Jan Deelmann, Culemborg, Netherlands; Michael Franz Lappert, Brighton, United Kingdom; Wing-Por Leung, Hong Kong; Hung-Kay Lee, Kowloon, both of The Hong Kong Special Administrative Region of the People's Republic of China

[73] Assignee: BASF Aktiengesellschaft, Ludwigshafen, Germany

[21] Appl. No.: 08/838,225

[22] Filed: Apr. 16, 1997

[30] Foreign Application Priority Data

Apr. 25, 1996 [DE] Germany ................. 196 16 523

[51] Int. Cl.$^7$ ................. C07F 7/00; C07F 9/00
[52] U.S. Cl. ................. 556/12; 556/42; 556/52; 534/15; 526/90; 526/122; 526/128; 526/144; 502/103; 502/117; 546/2; 548/402
[58] Field of Search ................. 556/42, 52, 12; 534/15; 502/103, 117; 526/90, 122, 128, 141; 546/2; 548/402

[56] References Cited

U.S. PATENT DOCUMENTS 4,794,096  12/1988  Ewen ................. 502/117

FOREIGN PATENT DOCUMENTS 0 284 708  10/1988  European Pat. Off. .
4202889    2/1992   Germany .
4218199    6/1992   Germany .
WO 91/09882  7/1991  WIPO .
WO 95/33776 12/1995  WIPO .

OTHER PUBLICATIONS

"Polyolefins", Ullmann's Encyclopedia Of Industrial Chemistry, 5. Ed., vol. A21, (pp. 502–504), 1992.

Michael F. Lappert, et al. "Recent Studies on Metal and Metalloid Bis(trimethylsilyl)methyls and the Transformation of the Bis(trimethylsilyl)methyl into the Azaallyl and Beta–Diketinimato Ligands", Journal Of Organometallic Chemistry 500, (pp. 203–217), 1995.

Rocco I. Papasergio, et al. "Lithiation of 2–Me$_3$SiCHRC$_5$H$_4$N(R=H or SiMe$_3$): Influence of Solvent on the Nature of the Product (from X–Ray Structure Determinations) and Asymmetric Induction. A Note on the Lithiation of Some Analogous 3—and 4–Methylpyridines", Journal of Chem. Soc. Dalton Trans., (pp. 1161–1172), 1990.

Hitchcock et al., *J. of Chem. Soc, Chem. Comm.*, vol. 17, Sep. 7, 1994, pp. 2637–2638.

Deelman et al., J. Organomet. Chem., vol. 513, No. 1–2, pp. 281–285, 1996.

*Primary Examiner*—Porfirio Nazario-Gonzalez
*Attorney, Agent, or Firm*—Keil & Weinkauf

[57] ABSTRACT

Transition metal complexes of the formula I $$L_mMX_n \qquad \qquad I,$$

where

L is a ligand of the formula II

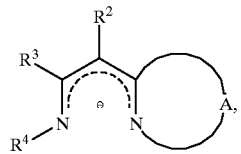

m is 1 or 2,

M is a titanium, zirconium, hafnium, vanadium, niobium, tantalum, or a rare earth metal, X is fluorine, chlorine, bromine, iodine, hydrogen, $C_1$–$C_{10}$-alkyl, $C_6$–$C_{15}$-aryl or $OR^1$, n is 1, 2, 3, or 4 as defined herein, and $R^1$, $R^2$, $R^3$, $R^4$, and A are as defined herein, and the use of these complexes as catalysts for olefin polymerization are described herein.

4 Claims, No Drawings

POLYMERIZATION CATALYSTS CONTAINING β-DIKETIMINATE LIGANDS

Polymerization catalysts containing β-diketiminate ligands

The present invention relates to transition metal complexes of the general formula I $$L_mMX_n \qquad I,$$

where the variables have the following meanings:

M is titanium, zirconium, hafnium, vanadium, niobium, tantalum or a rare earth metal, X is fluorine, chlorine, bromine, iodine, hydrogen, $C_1$–$C_{10}$-alkyl, $C_6$–$C_{15}$-aryl or $OR^1$, $R^1$ is $C_1$–$C_{10}$-alkyl, $C_6$–$C_{15}$-aryl, alkylaryl, arylalkyl, fluoroalkyl or fluoroaryl each having from 1 to 10 carbon atoms in the alkyl radical and from 6 to 20 carbon atoms in the aryl radical, m is 1 or 2, n is 4–m when M is titanium, zirconium or hafnium, or is 5–m when M is vanadium, niobium or tantalum, or is 3–m when M is a rare earth metal, and L is a ligand of the general formula II

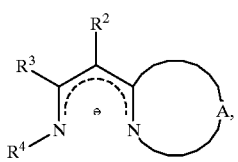

where

A is a bridge which together with the nitrogen and carbon atoms to which it is connected forms a five-membered or six-membered, unsubstituted or substituted aromatic ring which can also contain two further heteroatoms selected from the group consisting of oxygen, sulfur and nitrogen and can be fused to a further isoaromatic or heteroaromatic system having two, three or four rings, $R^2$ is hydrogen, $C_1$–$C_{10}$-alkyl, $C_6$–$C_{15}$-aryl, tri-($C_1$–$C_{10}$)alkylsilyl or tri-($C_6$–$C_{15}$)arylsilyl, $R^3$ is a $C_6$–$C_{15}$-aryl- or $C_1$–$C_{10}$-alkyl radical which bears no hydrogen on the β-carbon atom and $R^4$ is hydrogen, $C_1$–$C_{10}$-alkyl, $C_6$–$C_{15}$-aryl, tri-($C_1$–$C_{10}$)alkylsilyl or tri-($C_6$–$C_{15}$)arylsilyl.

The invention also relates to a process for preparing the transition metal complexes, β-diketimines whose anions serve as ligands for the transition metal complexes, the use of the transition metal complexes as catalysts for polymerizing olefins, a process for preparing polymers with the aid of these transition metal complexes, the use of the polymers for producing fibers, films and moldings and also such fibers, films and moldings themselves.

Transition metal complexes of elements of the 4th transition group of the Periodic Table have long been used as catalysts for olefin polymerization. Examples of known complexes are Ziegler catalysts and metallocene catalysts (see, for example, Ullmann's Encyclopedia of Industrial Chemistry, 5th Edition, Vol. A21, pp. 502–504 (1992)). Transition metal complexes having other ligand systems have also been used as catalysts, for example azaallyl complexes (WO 95/33776) and β-diketiminate complexes (J. Organometall. Chem., 500, 203–217 (1995)). However, the known catalyst systems still leave something to be desired in terms of their product specificity, in particular in respect of the chain length of the polymers.

It is an object of the present invention to provide novel transition metal complexes which are suitable as catalysts for olefin polymerization and overcome the disadvantages of the known catalysts.

We have found that this object is achieved by means of the transition metal complexes mentioned in the introduction.

The present invention also provides a process for preparing the transition metal complexes, β-diketimines whose anions serve as ligands for the transition metal complexes, the use of the transition metal complexes as catalysts for polymerizing olefins, a process for preparing polymers with the aid of these transition metal complexes, the use of the polymers for producing fibers, films and moldings and also such fibers, films and moldings themselves.

Among the transition metals M in the general formula I, preference is given to the elements of the 4th transition group of the Periodic Table, particularly preferably zirconium.

Particular examples of ligands X are the halogens fluorine, chlorine, bromine and iodine, with particular preference being given to chlorine. Particular examples of suitable $C_1$–$C_{10}$-alkyl radicals are methyl, ethyl, propyl and butyl. The preferred $C_6$–$C_{15}$-aryl radical is the phenyl radical.

In each case, the numbers m and n add up to the valence of the respective central transition metal atom. m is preferably 1 since transition metal complexes containing one β-diketiminate ligand display particularly good catalytic activity. This applies in particular to the metal complexes of titanium and zirconium. However, the preparation of the transition metal complexes usually first gives a complex having m=2 which is then reacted with $MX_{n+m}$ in a comproportionation reaction to give the complex $L_lMX_n$.

Suitable radicals $R^2$ in the ligand L of the general formula II are, for example, the alkyl radicals methyl, ethyl, n-propyl, isopropyl, n-butyl, isobutyl, sec-butyl, tert-butyl and also the various isomers of pentyl, hexyl, heptyl, octyl, nonyl and decyl.

Other suitable radicals $R^2$ are $C_6$–$C_{15}$-aryl radicals, in particular unsubstituted phenyl or naphthyl radicals or phenyl or naphthyl radicals substituted by alkyl radicals selected from the abovementioned group.

Further possible radicals $R^2$ are hydrogen, triphenylsilyl and trimethylsilyl.

Suitable radicals $R^3$ are, in particular, unsubstituted phenyl radicals or phenyl radicals substituted by methyl, ethyl or halogen, particularly preferably p-methylphenyl and pentafluorophenyl. Among the $C_1$–$C_{10}$-alkyl radicals which bear no hydrogen atom on the α-carbon atom, particular mention may be made of tert-butyl.

Suitable radicals $R^4$ are the same radicals as mentioned for $R^2$, preferably trialkylsilyl or triarylsilyl radicals, particularly preferably trimethylsilyl.

The bridge A is joined onto the group

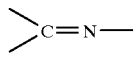

to form a five-membered or six-membered ring system. This ring system can bear two further heteroatoms so as to give, for example, ring systems from the pyridine, pyridazine, pyrimidine, pyrazine, triazine, pyrrole, pyrazole, thiazole or oxazole series. These ring systems can additionally be fused to a further isoaromatic or heteroaromatic system having two, three or four rings so as to give, for example, ring systems from the indole, indazole, quinoline, isoquinoline or quinazoline series.

Preferably, the bridge A is joined to the group

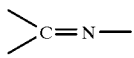

to form a pyridine, quinoline or isoquinoline ring system.

Preference is given to transition metal complexes in which A is a bridge of the general formula III

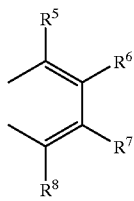

III where the substituents $R^5$, $R^6$, $R^7$, $R^8$ are hydrogen, $C_1$–$C_{10}$-alkyl, $C_6$–$C_{15}$-aryl or corresponding substituents bonded via oxygen, sulfur, nitrogen or phosphorus, nitro or nitroso.

The substituents $R^5$, R $R^7$ and $R^8$ are preferably hydrogen. Suitable alkyl and aryl radicals are, for example, the radicals mentioned under $R^2$. Other possible substituents are those in which hydrogen or the abovementioned alkyl or aryl radicals are bonded via oxygen, sulfur, nitrogen or phosphorus, for example alkoxy, alkylthio, monoalkylamino, dialkylamino, dialkylphosphino, aryloxy, arylthio, monoarylamino, diarylamino or diarylphosphino.

Preference is also given to transition metal complexes in which A is a bridge of the general formula IV

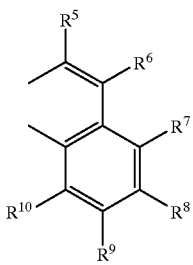

IV where the substituents $R^5$, $R^6$, $R^7$ and $R^8$ are as defined above and $R^9$ and $R^{10}$ likewise have these meanings.

For the substituents $R^9$ and $R^{10}$, the same preferences as have been stated for the radicals $R^5$ and $R^8$ apply.

To prepare the transition metal complexes of the present invention, we have found a process which comprises converting a compound of the general formula V

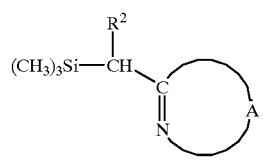

V by means of a strong base into the anion Va

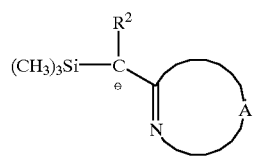

Va reacting this with a nitrile $R^3$—CN to give the anion IIa

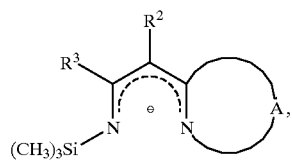

IIa if desired replacing the protective group $(CH_3)_3Si$— by reaction with a compound $R^4$-halogen and reacting the resulting anion II

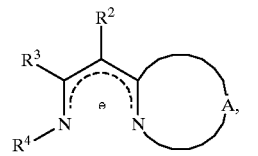

II with a transition metal compound of the formula $MX_{m+n}$.

The starting compounds V can be obtained in a known manner. The preparation is described, for example, in J. Chem. Soc., Dalton Trans. 1990, 1161.

An example of a strong base for converting V into the anion Va is butyllithium. (The counterion, in this case $Li^\oplus$, was not shown in the reaction scheme in the interest of clarity).

The reaction conditions are not critical per se.

Carrying out the preparation in a hexane/diethyl ether mixture as solvent at about 20° C. under a protective gas atmosphere of nitrogen or argon has been found to be particularly useful.

Protonation of the anions II, for example in the presence of water, gives the β-diketimines of the general formula IIb

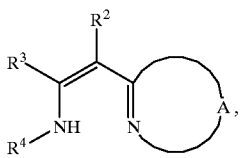

where the variables are as defined above. These β-diketimines are stable on storage and are valuable intermediates for preparing the transition metal complexes of the present invention.

The transition metal complexes of the present invention are used as catalysts for polymerizing olefins.

Preferred polymerizable olefins are ethylene, propylene, but-1-ene, pent-1-ene, hex-1-ene, oct-1-ene and mixtures of these.

In the process of the present invention for preparing polymers of $C_2$–$C_{10}$-alk-1-enes at pressures of from 0.5 to 3000 bar and at from −50 to 300° C. using a catalyst system, the catalyst system comprises as active constituents a) transition metal complexes having the formula I

    I, and b$_1$) an open-chain or cyclic aluminoxane compound of the general formula VI or VII

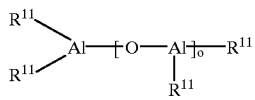 VI

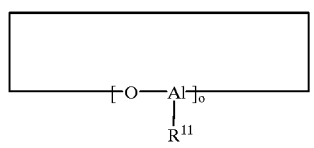 VII where $R_{11}$ is $C_1$–$C_4$-alkyl and o is from 5 to 30 and/or
b$_2$) cation-forming compounds.

The radical $R^{11}$ is preferably methyl or ethyl, o is preferably from 10 to 25.

The oligomeric aluminoxane compounds are usually prepared by reacting a solution of trialkylaluminum with water and is, for example, described in EP-A 284 708 and U.S. Pat. No. 4,794,096.

The oligomeric aluminoxane compounds thus obtained are usually in the form of mixtures of chain molecules of various lengths, both linear and cyclic, so that m is to be regarded as a mean value. The aluminoxane compounds can also be present in admixture with other metal alkyls, preferably aluminum alkyls.

It has been found to be advantageous to use the transition metal complexes of the present invention and the oligomeric aluminoxane compound in such amounts that the atom ratio of aluminum from the oligomeric aluminoxane compound and the transition metal is in the range from 10:1 to $10^6$:1, in particular in the range from 10:1 to $10^4$:1.

Suitable cation-forming compounds are, in particular, strong, uncharged Lewis acids, ionic compounds having Lewis-acid cations and ionic compounds having Brönsted acids as cation.

As strong, uncharged Lewis acids, preference is given to compounds of the general formula VII

 VII where
$M^1$ is an element of main group III of the Periodic Table, in particular B, Al or Ga, preferably B,
$X^1$, $X^2$ and $X^3$ are hydrogen, $C_1$–$C_{10}$-alkyl, $C_6$–$C_{15}$-aryl, alkylaryl, arylalkyl, haloalkyl or haloaryl each having from 1 to 10 carbon atoms in the alkyl radical and from 6 to 20 carbon atoms in the aryl radical or fluorine, chlorine, bromine or iodine, in particular haloaryls, preferably pentafluorophenyl.

Particular preference is given to compounds of the general formula VII in which $X^1$, $X^2$ and $X^3$ are identical, preferably tris(pentafluorophenyl)borane.

Suitable ionic compounds having Lewis-acid cations are compounds of the general formula VIII

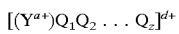 VIII, where
Y is an element of main groups I to VI or transition groups I to VIII of the Periodic Table,
$Q_1$ to $Q_Z$ are singly negatively charged radicals such as $C_1$–$C_{28}$-alkyl, $C_6$–$C_{15}$-aryl, alkylaryl, arylalkyl, haloalkyl, haloaryl each having from 6 to 20 carbon atoms in the aryl radical and from 1 to 28 carbon atoms in the alkyl radical, $C_1$–$C_{10}$-cycloalkyl which can be unsubstituted or substituted by $C_1$–$C_{10}$-alkyl groups, halogen, $C_1$–$C_{28}$-alkoxy, $C_6$–$C_{15}$-aryloxy, silyl or mercaptyl groups,
a is an integer from 1 to 6,
z is an integer from 0 to 5,
d is the difference a–z, where d is, however, greater than or equal to 1.

Carbonium cations, oxonium cations and sulfonium cations as well as cationic transitiol metal complexes are particularly suitable. Particular mention may be made of the triphenylmethyl cation, the silver cation and the 1,1'-dimethylferrocenyl cation. Preferably, they have counterions which do not coordinate, in particular boron compounds as are also mentioned in WO 91/09882, preferably tetrakis (pentafluorophenyl)borate.

Ionic compounds having Brönsted acids as cations and preferably counterions which likewise do not coordinate are mentioned in WO 91/09882; the preferred cation is N,N-dimethylanilinium.

The amount of cation-forming compounds is preferably from 0.1 to 10 equivalents, based on the transition metal complex I.

Solvents used for these catalyst systems are customary aromatic hydrocarbons, preferably having from 6 to 20 carbon atoms, in particular xylenes and toluene and mixtures thereof.

In the preparation of the polymers of $C_2$–$C_{10}$-alk-1-enes, it is also possible to use a supported catalyst system. Suitable support materials are, for example, silicas, preferably those of the formula $SiO_2 \cdot a\,Al_2O_3$, where a is in the range from 0 to 2, preferably from 0 to 0.5; these are thus aluminosilicates or silicon dioxide. The supports preferably have a particle diameter in the range from 1 to 200 μm, in particular from 30 to 80 μm. Such products are commercially available, eg. Silica Gel 332 from Grace.

For the purposes of the present invention, polymers of $C_2$–$C_{10}$-alk-1-enes are homopolymers or copolymers of $C_2$–$C_{10}$-alk-1-enes, in particular of $C_2$–$C_6$-alk-1-enes. Preference is given to homopolymers of ethylene or of propylene and copolymers of ethylene and propylene, ethylene and but-1-ene, ethylene and pent-1-ene, ethylene and hex-1-ene or propylene and but-1-ene, propylene and pent-1-ene or else propylene and hex-1-ene. The proportion of comonomers can here be up to 50% by weight, in particular up to 30% by weight.

The process of the present invention can be carried out either in solution, in suspension, in the gas phase or else as a bulk polymerization. Preference is given to carrying out the process for preparing the polymers of $C_2$–$C_{10}$-alk-1-enes in the gas phase. The polymerization conditions are not critical per se; pressures of from 0.5 to 3000 bar, preferably from 1 to 80 bar, and temperatures of from −50 to +300° C., preferably from 0 to 150° C., have been found to be useful. The polymerization can be carried out in the presence of customary regulators, for example hydrogen or $C_2$–$C_8$-alk-1-enes, and in customary polymerization reactors.

In a preferred process for preparing homopolymers of $C_2$–$C_{10}$-alk-1-enes, the active constituents of the catalyst system are initially charged in toluene at temperatures in the range from 0 to 140° C.

This initial charge is then pressurized with from 1 to 60 bar of the $C_2$–$C_{10}$-alk-1-ene over a period of from 0.5 to 12 hours. The work-up of the polymers is then carried out by conventional methods.

The process of the invention for preparing polymers of $C_2$–$C_{10}$-alk-1-enes is simple to carry out.

The polymers of $C_2$–$C_{10}$-alk-1-enes prepared by the process of the present invention have a balanced property profile. In particular, the polymers have very high molecular weights and are suitable for producing fibers, films and moldings.

EXAMPLES

Example 1

Synthesis of [Li{N(SiMe$_3$)C(Ph)C(H)(C$_5$H$_4$N-2)}]$_2$

[Li{CH(SiMe$_3$)(C$_5$H$_4$N-2)}]$_2$ was prepared by adding, at room temperature, 5.13 g (31 mmol) of CH$_2$(SiMe$_3$)(C$_5$H$_4$N-2) to a solution of n-butyllithium (32 mmol) in 20 ml of hexane and 20 ml of diethyl ether. After stirring the reaction mixture for 30 minutes at room temperature, the suspension was diluted with 35 ml of diethyl ether. 3.3 ml (32 mmol) of benzonitrile were then added dropwise at room temperature. The reaction mixture was stirred for 16 hours and the volatile constituents were then removed under reduced pressure. The residue was dried at 50° C. under reduced pressure. Crystals were obtained by slow cooling of a hot hexane solution (50 ml) to 0° C. Yield: 2.89 g (34%)

$^1$H NMR (360 MHz, C$_6$D$_6$): δ 8.05 (m, 1H, py), 790 (d, J=7.4 Hz, 2H, Ph), 7.29 (t, J=7.4, 2H, Ph), 7.20 (d, J=7.2, 1H, py), 6.99 (t, J=7.8, 1H, Ph), 6.73 (d, J=7.9 Hz, 1H, py), 6.41 (ps, t, 1H, py), 6.24 (s, 1H, CH), −0.02 (s, 9H, SiMe$_3$). $^{13}$C NMR (62.9 MHz, C$_6$D$_6$/C$_6$D$_6$): δ 165.3 (NCPh), 160.5, 148.5, 147.2, 137.3, 129.2, 128.2, 127.9, 124.1 and 117.6 (aryl C), 107.1 (CH), 2.5 (SiMe$_3$).

Example 2

Synthesis of [Li{N(SiMe$_3$)C(Ph)C(SiMe$_3$)(C$_5$H$_4$N-2)}]$_2$

[Li{C(SiMe$_3$)$_2$(C$_5$H$_4$N-2)}]$_2$ was prepared by adding, at room temperature, 8.0 ml (7.4 g, 31 mmol) of CH(SiMe$_3$)$_2$(C$_5$H$_4$N-2) to a solution of n-butyllithium (32 mmol) in 20 ml of hexane and 50 ml of diethyl ether. The reaction mixture was stirred for 1 hour at room temperature. 3.2 ml (31 mmol) of benzonitrile were then added dropwise at room temperature. The reaction mixture was stirred for 15 hours and the volatile constituents were then removed under reduced pressure. The residue was suspended in 50 ml of hexane, cooled to −30° C. and then collected on a frit. The product was washed with 30 ml of pentane. Yield: 7.37 g (68%)

$^1$H NMR (250 MHz, C$_4$D$_8$O): δ 8.13 (ddd, J=5.2, 2.0, 0.9 Hz, 1H, py), 7.38 (ddd, J=8.3, 7.1, 2.0 Hz, 1H, py), 7.33–7.29 (m, 2H, Ph), 7.18–7.15 (m, Ph), 7.11 (dt, J=8.3, 1.0 Hz, 1H, py), 6.68 (ddd, J=7.1, 5.2, 1.2 Hz, 1H, py), −0.36 (s, 9H, SiMe$_3$), −0.41 (s, 9H, SiMe$_3$). $^{13}$C NMR (62.9 MHz, C$_4$D$_8$O): δ 174.2 (NCPh), 167.0, 151.5, 146.4, 135.0, 130.8, 127.6, 127.2, 125.8 and 115.7 (aryl C), 99.0 (CSiMe$_3$), 3.8 (SiMe$_3$).

Example 3

Synthesis of [Li{N(SiMe$_3$)C(Ph)C(SiMe$_3$)(C$_9$H$_6$N-2)}]$_2$

CH$_2$(SiMe$_3$)(C$_9$H$_6$N-2) (0.9 ml, 4.1 mmol) were added dropwise at 0° C. to a solution of n-butyllithium (2.5 ml, 4.0 mmol) in hexane diluted with 5 ml of diethyl ether. The solution was stirred for 30 minutes at room temperature and 0.5 ml (4.0 mmol) of SiMe$_3$Cl were then added. After stirring for 15 hours at room temperature, the suspension was filtered and admixed at 0° C. with 2.4 ml (3.8 mmol) of n-butyllithium. The solution was stirred for 15 minutes at room temperature and 0.4 ml (3.9 mmol) of benzonitrile were then added at 0° C. After the reaction mixture had been stirred for 15 hours, the volatile constituents were removed under reduced pressure and the residue was dried under reduced pressure for 30 minutes at 50° C. The residue was washed twice with 10 ml of hexane each time. Yield: 1.02 g (64%) $^1$H NMR (250 MHz, C$_4$D$_8$O): δ 7.80 (t, J=9.0 Hz, 2H, qui), 7.60 (dd, J=7.9, 1.2 Hz, 1H, Ph), 7.45 (m, 1H,Ph), 7.34 (m, 3H, aryl H), 7.20 (m, 4H, aryl H), −0.32 (s, 9H, SiMe$_3$), −0.38 (s, 9H, SiMe$_3$) $^{13}$C NMR (62.9 MHz, C$_4$H$_8$O): δ 174.8, (NCPh), 167.7, 151.2, 148.6, 133.7, 130.9, 128.5, 128.0, 127.7, 127.5, 127.4, 126.8, 125.9 and 123.2 (aryl C), 100.6 (CSiMe$_3$), 4.1 (SiMe$_3$), 3.8 (SiMe$_3$).

Example 4

Synthesis of Zr{N(SiMe$_3$)C(Ph)C(H)(C$_5$H$_4$N-2)}$_2$Cl$_2$

A solution of 2.38 g (4.34 mmol) of the compound from Example 1 in 12 ml of THF was added at 0° C. to a solution of 0.99 g (4.25 mmol) of ZrCl$_4$ in 60 ml of THF. The reaction mixture was allowed to warm up to room temperature, then stirred for 15 hours and subsequently refluxed for 1.5 hours. The volatile constituents were removed under reduced pressure and the residue was extracted with 10 ml of hexane, 50 ml of diethyl ether and dichloromethane (2×25 ml). The combined extracts were concentrated to 50 ml and subsequently cooled to −30° C. The crystals thus obtained were washed with 5 ml of hexane. Yield: 1.58 g (53%).

$^1$H NMR (360 MHz, C$_6$D$_6$): δ9.04 (d, J=6.0 Hz, 2H, py), 7.66 (d, J=7.2 Hz, 4H, Ph), 7.1–7.0 (m, 6H, Ph), 6.77 (t, J=7.7 Hz, 2H, py), 6.35 (d, J=7.9 Hz, 2H, py), 6.30 (t, J=6.6, 2H, py), 6.05 (s, 2H, CH), 0.21 (s, 18H, SiMe$_3$). $^{13}$C NMR (62.9 MHz, C$_6$D$_6$): δ 155.0 (NCPh), 154.2, 149.8, 141.2, 138.0, 129.2, 128.8, 127.9, 123.3 and 120.2 (aryl C), 111.2 (CH), 3.1 (SiMe$_3$).

Example 5

Synthesis of Zr{N(SiMe$_3$)C(Ph)C(SiMe$_3$)(C$_5$H$_4$N-2)}$_2$Cl$_2$ 3.86 g (5.70 mmol) of the compound from Example 2 were added to a solution of 1.33 g (5.71 mmol) of ZrCl$_4$ in 60 ml of diethyl ether. The reaction mixture was stirred for 16 hours and the volatile constituents were then removed under reduced pressure. The residue was extracted with 2×50 ml of dichloromethane and filtered off twice. The volatile constituents were removed under reduced pressure and the residue was recrystallized at −30° C. from 50 ml of toluene. Yield: 1.32 g (1.57 mmol). Concentration of the mother liquor gave a further 1.13 g of product. Total yield: 2.45 g (54%).

$^1$H NMR (360 MHz, $C_6D_6$): δ 8.59–8.58 (m, 2H, py), 7.68 (D, J=5.7 Hz, 2H, Ph), 7.63 (d, J=6.6 Hz, 2H, Ph), 7.28 (d, J=8.1 Hz, 2H, py), 7.12 (m, 6H, Ph), 6.87 (td, J=7.7 Hz, 1.7 Hz, 2H, py), 6.00 (t, J=6.0 Hz, 2H, py), 0.03 (s, 18H, $SiMe_3$), 0.01 (s, 18H, $SiMe_3$). $^{13}$C NMR (62.9 Hz, $C_6D_6$): δ 165.0 (NCPh), 162.9, 149.8, 143.4, 137.9, 130.4, 129.3, 128.6, 128.4, 128.3, 127.9, 127.0 and 125.8 (aryl C), 118.6 and 118.3 ($CSiMe_3$), 4.3 and 2.3 ($SiMe_3$).

Example 6
Synthesis of $Zr\{N(SiMe_3)C(Ph)C(SiMe_3)(2-C_9H_6N)\}_2Cl_2$ 1.7 g (4.3 mmol) of the compound from Example 3 were added to a suspension of 0.5 g (2.2 mmol) of $ZrCl_4$ in 50 ml of diethyl ether. The reaction mixture was stirred for 3 hours and the volatile constituents were then removed under reduced pressure. The residue was extracted with 45 ml of warm toluene and filtered off. The filtrate was evaporated to dryness under reduced pressure and the residue was extracted with 25 ml of hexane. The solid was recrystallized from a mixture of dichloromethane and diethyl ether (1:1, v:v). Yield: 0.78 g (37%).

$^1$H NMR (360 MHz, $C_6D_6$): δ 8.82 (d, J=8.3 Hz, 2H, qui), 8.28 (d, J=8.4 Hz, 2H, qui), 7.80 (d, =6.9 Hz, 2H, Ph), 7.54 (d, J=8.6 Hz, 2H, Ph), 7.26–7.17 (m, 8H, Ph and qui), 6.77–6.75 (m, 2H, qui, 6.60–6.57 (m, 4H, qui), 0.09 (s, 18H, $SiMe_3$), 0.08 (s, 18H, $SiMe_3$). $^{13}$C NMR (62.9 MHz, $C_6D_6$/$C_6H_6$): δ 166.5 (NCPh), 163.5, 145.8, 142.8, 138.7, 135.1, 131.5, 130.7, 129.8, 127.3, 126.9, 126.5, 124.9, 119.5 and 118.4 (aryl C), 104.9 ($CSiMe_3$), 3.9 and 2.6 ($SiMe_3$).

Example 7
Synthesis of $Zr\{N(SiMe_3)C(Ph)C(SiMe_3)(2-C_9H_6N)\}Cl_3$ 2.16 g (2.57 mmol) of the compound from Example 5 were added to a suspension of 0.63 g (2.7 mmol) of $ZrCl_4$ in 35 ml of toluene. The reaction mixture was stirred for 16 hours and the volatile constituents were then removed under reduced pressure. The residue was extracted with 20 ml of hexane. Yield: 1.73 g (3.22 mmol, 63%).

$^1$H NMR (360 MHz, $CD_2Cl_2$): δ 8.88 (d, J=5.4 Hz, 1H, py), 8.36 (t, J=8.1 Hz, 1H, py), 7.29 (d, J=8.1 Hz, 1H), 7.73–7.42 (6H, Ph and py), −0.09 (S, 9H, $SiMe_3$), −0.28 (s, 9H, $SiMe_3$).

Example 8
Synthesis of $Zr\{N(SiMe_3)C(Ph)C(SiMe_3)(2-C_9H_6N)\}Cl_3$ 1.53 g (1.63 mmol) of the compound from Example 6 were added to a suspension of 0.39 g (1.67 mmol) of $ZrCl_4$ in 25 ml of dichloromethane. The reaction mixture was stirred for 16 hours, then filtered and the filtrate was concentrated to 10 ml. Cooling the solution to −30° C. gave 0.81 g of crystals. More of the substance could be isolated from the mother liquor. Total yield: 1.10 g (57%).

$^1$H NMR (360 MHz, $CD_2Cl_2$): δ 8.80 (d,.J=8.7 Hz, 1H, qui), 8.75 (d, J=8.4 Hz, 1H, qui), 8.0–7.5 (14H, Ph and qui), 7.40 (t, J=7.5 Hz, 1H), 7.25 (t, J=7.7 Hz, 1H), 6.95 (t, J=7.3 Hz, 1H), 6.86 (t, J=7.6 Hz, 1H), 6.65 (d, J=8.4 Hz, 1H, qui), 6.34 (d, J=8.6 Hz, 1H qui), 0.26 (s, 9H, $SiMe_3$), −0.10 (s, 9H, $SiMe_3$), −0.20 (s, 9H, $SiMe_3$), −0.31 (s, 9H, SiMe3).

Example 9
Ethylene polymerization

In a typical experiment, 31 mg (0.053 mmol) of the compound from Example 8 were reacted at room temperature with 3.5 ml (5.4 mmol of Al) of a 10% strength by weight solution of methylaluminoxane (MAO) in toluene. The solution was diluted with 31.5 ml of toluene, degassed and then placed at room temperature under a pressure of 1.5 bar of ethylene. After 30 minutes, the polymerization was stopped by addition of methanolic HCl. The polymer was isolated, washed with 1 M HCl solution, water and methanol and then dried to constant weight at 80° C. Further examples carried out in a similar manner are shown in Table 1.

TABLE 1

| Ethylene polymerization: | | | | | | |
|---|---|---|---|---|---|---|
| Catalyst from Example | Weight of catalyst (mg) | MAO solution (ml) | Toluene added (ml) | Reaction time (min) | Yield of PE (mg) | η value (dl/g) |
| 4 | 50 | 5 | 20 | 60 | 10 | 11.2 |
| 7 | 41 | 5 | 45 | 25 | 620 | 9.1 |
| 8 | 31 | 3.5 | 32 | 25 | 150 | 7.3 |

The η values were determined in accordance with ISO 1628-3.

We claim:

1. A transition metal complex of the general formula I $$L_mMX_n \qquad\qquad I,$$

where the variables have the following meanings:

M is titanium, zirconium, hafnium, vanadium, niobium, tantalum or a rare earth metal, X is fluorine, chlorine, bromine, iodine, hydrogen, $C_1$–$C_{10}$-alkyl, $C_6$–$C_{15}$-aryl or $OR^1$, $R^1$ is $C_1$–$C_{10}$-alkyl, $C_6$–$C_{15}$-aryl, alkylaryl, arylalkyl, fluoroalkyl or fluoroaryl each having from 1 to 10 carbon atoms in the alkyl radical and from 6 to 20 carbon atoms in the aryl radical, m is 1 or 2, n is 4−m when M is titanium, zirconium or hafnium, or is 5−m when M is vanadium, niobium or tantalum, or is 3−m when M is a rare earth metal, and L is a ligand of the general formula II

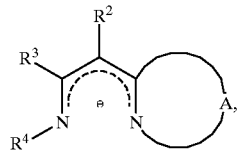

where

A is a bridge which together with the nitrogen and carbon atoms to which it is connected forms a five-membered or six-membered, unsubstituted or substituted aromatic ring which can also contain two further heteroatoms selected from the group consisting of oxygen, sulfur and nitrogen and can be fused to a further isoaromatic or heteroaromatic system having two, three or four rings, $R^2$ is hydrogen, $C_1$–$C_{10}$-alkyl, $C_6$–$C_{15}$-aryl, tri-($C_1$–$C_{10}$)alkylsilyl or tri-($C_6$–$C_{15}$)arylsilyl, $R^3$ is a $C_6$–$C_{15}$-aryl-, $C_6$–$C_{15}$-fluoroaryl-,$C_1$–$C_{10}$-alkyl or $C_1$–$C_{10}$-fluoroalkyl radical which bears no hydrogen on the α-carbon atom and $R^4$ is hydrogen, $C_1$–$C_{10}$-alkyl, $C_6$–$C_{15}$-aryl, tri-($C_1$–$C_{10}$)alkylsilyl or tri-($C_6$–$C_{15}$)arylsilyl.

2. A transition metal complex as claimed in claim 1 in which A is a bridge of the general formula III

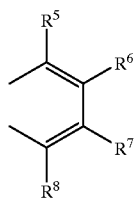
III where the substituents

R⁵, R⁶, R⁷, R⁸ are hydrogen, $C_1$–$C_{10}$-alkyl, $C_6$–$C_{15}$-aryl or corresponding substituents bonded via oxygen, sulfur, nitrogen or phosphorus, nitro or nitroso.

3. A transition metal complex as claimed in claim 1 in which A is a bridge of the general formula IV

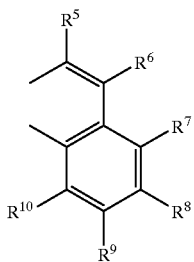
IV where the substituents $R^5$, $R^6$, $R^7$ and $R^8$ are as defined above and $R^9$ and $R^{10}$ likewise have the same meanings.

4. A process for preparing a transition metal complex as claimed in claim 1, which comprises converting a compound of the general formula V

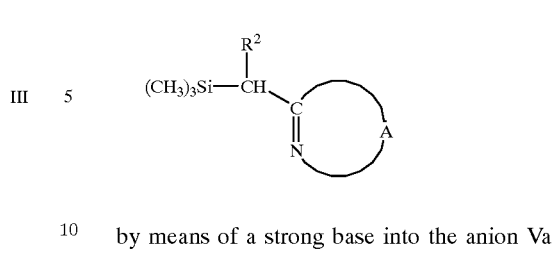
V by means of a strong base into the anion Va

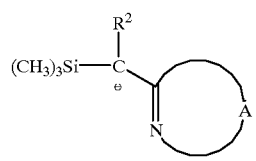
Va reacting this with a nitrile R³—CN to give the anion IIa

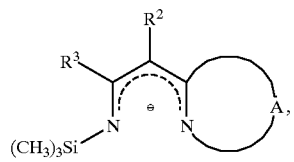
IIa if desired replacing the protective group $(CH_3)_3Si$— by reaction with a compound $R^4$-halogen and reacting the resulting anion II

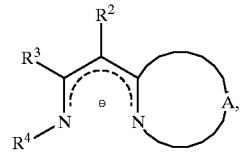
II with a transition metal compound of the formula $MX_{m+n}$.

* * * * *